United States Patent
Sovak et al.

(10) Patent No.: US 7,763,288 B2
(45) Date of Patent: Jul. 27, 2010

(54) SKIN CARE COMPOSITIONS AND METHODS

(75) Inventors: Milos Sovak, Rancho Santa Fe, CA (US); Allen L. Seligson, Ramona, CA (US); Jiri Prokop, Prague (CZ)

(73) Assignee: Biophysica, Inc., La Jolla, CA (US)

( * ) Notice: Subject to any disclaimer, the term of this patent is extended or adjusted under 35 U.S.C. 154(b) by 0 days.

(21) Appl. No.: 12/134,762

(22) Filed: Jun. 6, 2008

(65) Prior Publication Data

US 2008/0260875 A1 Oct. 23, 2008

Related U.S. Application Data

(62) Division of application No. 11/509,485, filed on Aug. 24, 2006, now abandoned.

(60) Provisional application No. 60/713,882, filed on Sep. 1, 2005.

(51) Int. Cl.
*A61K 36/00* (2006.01)
*A61K 36/87* (2006.01)
*A61K 8/02* (2006.01)
*A61K 36/31* (2006.01)

(52) U.S. Cl. ............... 424/725; 424/755; 424/401; 424/766

(58) Field of Classification Search .................. None
See application file for complete search history.

(56) References Cited

U.S. PATENT DOCUMENTS

| | | | |
|---|---|---|---|
| 5,889,054 | A | 3/1999 | Yu et al. |
| 6,139,829 | A | 10/2000 | Estrin |
| 6,180,133 | B1 | 1/2001 | Quan |
| 6,184,249 | B1 | 2/2001 | Sovak |
| 6,472,415 | B1 | 10/2002 | Sovak et al. |
| 6,551,656 | B1 | 4/2003 | Clough |
| 6,589,516 | B1 | 7/2003 | Eyre et al. |
| 2004/0009241 | A1 | 1/2004 | Inomata et al. |
| 2004/0014732 | A1* | 1/2004 | Sovak et al. ............. 514/169 |
| 2004/0191330 | A1 | 9/2004 | Keefe et al. |
| 2005/0025737 | A1 | 2/2005 | Sebagh |
| 2005/0048105 | A1 | 3/2005 | McNulty et al. |
| 2005/0048138 | A1 | 3/2005 | Perrier et al. |
| 2005/0123559 | A1 | 6/2005 | Majeed et al. |
| 2006/0286046 | A1* | 12/2006 | Haber .................... 424/59 |

FOREIGN PATENT DOCUMENTS

| | | |
|---|---|---|
| CN | 1137389 A | 12/1996 |
| JP | 2005060334 A | 3/2005 |
| WO | WO 01/17495 | 3/2001 |
| WO | WO 01/30314 | 5/2001 |
| WO | WO 01/58854 | 8/2001 |
| WO | WO 2004/026222 | 4/2004 |

OTHER PUBLICATIONS

Cha et al, Comparison of antioxidant activity and composition in Glycine max Merr. And Glycine soja Siebold et Zucc, Saengyak Hakhoechi (1996), 27 (3): 190-195.*

Petta et al, Genotoxicity induced by saponified coconut oil surfactant in prokaryote systems, Mutagenesis 19 (6): 441-444, 2004.*

D. Cousty-Berlin, et al., "Preliminary Pharmacokinetics and Metabolism of Novel Non-steroidal Antiandrogens in the Rat: Relation of their Systemic Activity to the Formation of a Common Metabolite," *J. Steroid Biochem. Molec. Biol*, 1994, vol. 51, No. ½, 47-55.

Herbert P. Goodheart, "Hirsutism Pathogenesis and causes," *Women's Health in Primary Care*, May 2000, vol. 3, No. 5, 329-337.

Milos Sovak, et al., "Fluridil, a Rationally Designed Topical Agent for Androgenetic Alopecia: First Clinical Experience," *Dermatol Surg*, 2002, 28:678-685.

Donald W. Shenenberger, et al., "Removal of Unwanted Facial Hair," *American Family Physician*, Nov. 2002, vol. 66, No. 10. [What pages are cited for this? -wd].

Ricardo Azziz, "The Evaluation and Management of Hirsutism," *The American College of Obstetricians and Gynecologists*, May 2003, vol. 101, No. 5, Part 1, 995-1007.

Allen L. Seligson, et al., "Development of Fluridil, a Topical Suppressor of the Androgen Receptor in Androgenetic Alopecia," *Drug Development Research*, 2003, 59:292-306.

Sator P-G, et al., "Skin aging and sex hormones in women—clinical perspectives for intervention by hormone replacement therapy," *Experimental Dermatology*, Dec. 2004, 13 (suppl. 4):36-40.

Rodney P. R. Dawber, "Guidance for the management of hirsutism," *Current Medical Research and Opinion*, Jul. 2005, vol. 21, No. 8, 1227-1234.

Shari B. Clarke, "Pharmacologic Modulation of Sebaceous Gland Activity: Mechanism and Clinical Applications," *Dermatol Clin*, 2007, vol. 25, 137-146.

Naoko Kanda, et al., "Regulatory roles of sex hormones in cutaneous biology and immunology," *Journal of Dermatological Science*, 2008, vol. 38, 1-7.

Jerry L. Mccullough, et al., "Prevention and Treatment of Skin Aging," *Ann. N.Y. Acad. Sci.*, 2006, vol. 1067, 323-331.

Written Opinion of the International Searching Authority, Mar. 17, 2007.

* cited by examiner

*Primary Examiner*—Qiuwen Mi

(57) ABSTRACT

Skin care compositions and methods are provided comprising a highly hydrophobic substance, an alkaryl polyfluorocarbon, particularly a substituted phenyl-polyfluoroacylamino propanamide, an alkanol and refined oils and the oil triglyceride fractions in sufficient amount to provide substantial homogeneity. When employed for hirsutism, optionally antioxidants and moisturizer are added. For use against wrinkles, additionally vitamins, antioxidants and a mixture of extracts of naturally occurring substances are present.

14 Claims, No Drawings

SKIN CARE COMPOSITIONS AND METHODS

CROSS-REFERENCE TO RELATED APPLICATIONS

This application is a divisional of U.S. application Ser. No. 11/509,485, filed Aug. 24, 2006, now abandoned, which is hereby incorporated by reference in its entirety. This application and U.S. application Ser. No. 11/509,485 claim priority from U.S. Provisional Patent Application No. 60/713,882 filed on Sep. 1, 2005, which is also hereby incorporated by reference in its entirety.

STATEMENT OF GOVERNMENTAL SUPPORT

This invention was not made with Government Support.

REFERENCE TO SEQUENCE LISTING, COMPUTER PROGRAM, OR COMPACT DISK

None.

BACKGROUND OF THE INVENTION

1. Field of the Invention

The field of this invention concerns cosmetic compositions, particularly skin care related to skin hormonal imbalance.

2. Related Art

Mammalian skin and associated characteristics, such as wrinkles and hair growth and loss, are significantly affected by hormones, and the individual skin responsiveness to their levels and ratios, since there is substantial interest in the treatment of skin and its associated characteristics, there have been numerous reports of treatment as palliatives and cures.

1. Wrinkle Reduction:

Wrinkles are skin folds and creases caused by dermal thinning and loss of elasticity, which is a result of the aging process and/or exposure to noxious substances and/or physical factors such as UV radiation, all of which adversely affect the skin metabolism. Wrinkles are not a medical condition and as long as the substances employed to treat them are not systemically resorbed and systemically active, the preparations fall into the field of cosmetics.

There are many claims to inventions for non-surgical wrinkle reduction or removal, but there are few systematic studies to support such claims. There is a plethora of facial creams available containing a variety of substances, many of which are either inefficient or induce side effects at the levels of efficacy. Thus, it is known that topical vitamin C, tretinoin, or isotretinoin, while transiently improving the wrinkles caused by aging and photo damage, have a considerable incidence of irritation. Inducing paresis of the muscle fibers for cosmetic purposes by substances blocking the neuromuscular junctions is not physiologically acceptable and has its own particular toxicity.

Topical and/or systemic application of estrogens of human origin have been shown to increase the skin collagen content and thus increase skin thickness as well as the concentration of skin mucopolysaccharides, which directly reduces the wrinkles' depth. However, giving mammalian estrogens systemically for the sole purpose of reducing the signs of skin aging would not be medically defensible. Dermatologists have explored topical estriol and 17-β-estradiol and found reduction in the wrinkle depth and increased hydration, but also, albeit to a degree, a systemic resorption resulting in a rise in prolactin (Schmidt et al., 1996 Int J Dermatol 35(9): 669-74). Therefore, topical mammalian estrogens for skin regeneration, although effective, cannot qualify as a cosmetic preparation and are not authorized in cosmetic creams. Certain phytoestrogens, especially the isoflavones, which are found in a variety of plants, as are the flavonoids, were shown to have a much lower effect than the mammal estrogens. However, in a topical application they are not resorbed systemically (Bayerl and Keil, 2002 Akt Dermatol 28:14-8).

There are many combinations of different ingredients in cosmetics, such as antioxidants, enzymes, phytoestrogens, emollients, humectants, and the like. Their ability to protect the skin and reduce the formation of wrinkles varies with the composition and its ingredients.

There is, therefore, a need for a safe, effective cosmetic that reduces wrinkling, has minimal or no side effects, such as erythema, edema or irritation, is not systemically resorbed when applied to the skin and does not result in a change in the skin coloration, e.g., is substantially transparent when applied.

2. Compositions Affecting Female Facial Hair Growth (Idiopathic Hirsutism):

Approximately eight percent of women are affected by idiopathic hirsutism (IH), i.e., excessive male-like pattern hair growth without underlying systemic endocrine pathology. IH is characterized either by higher sensitivity of the hair follicle androgen receptors to the androgens or by higher skin androgen levels. IH is considered a skin hyperandrogenetic syndrome in the cosmetic category since especially dark excessive facial hair is visible and leads to psychological distress.

The current treatment is topical and/or systemic pharmacological, combined with mechanical removal including shaving, depilatories, waxing, plucking, laser, intense pulsed light, and/or electrolysis. Metformin, primarily an antidiabetic treatment, known to be often associated with adverse gastrointestinal effects, is indicated only when IH is concomitant.

The androgen-targeting drugs improve female IH either by suppression of the male hormone synthesis such as by inhibiting 5-α reductase conversion of testosterone to dihydrotestosterone (by finasteride), or by blocking the androgen receptors. Finasteride and antiandrogens are contra-indicated in women of childbearing age as they can cause feminization of the male fetus. Cyproterone acetate (CPA), a progestagen with anti-androgenic properties, carries the risk of hypertension, thromboembolism, diabetes mellitus, hypercholesterolemia and endometrial cancer. An antiandrogen of steroidal structure for topical use was recently published (see Labrie et al.). Non-steroidal blocking agents of the androgen receptor, such as flutamide or bicalutamide, prevent the androgen binding. When tested topically in male androgenetic alopecia they proved to be substantially systemically resorbed; they are not approved for IH therapy. The antiandrogens, RU 58841 and RU 56187, i.e., N-substituted aryl hydantoins or thiohydantoins were tested topically; they are nevertheless converted systemically into a common metabolite, which is strongly antiandrogenic. Topical eflornithine inhibits ornithine decarboxylase and thus the conversion of ornithine to putrescine, which regulate the anagen phase of the hair growth.

Mechanical depilation by tweezing and depilatory can potentially exacerbate IH by stimulating the growth of thicker and coarser hair, making subsequent treatments more difficult and occasionally inducing folliculitis and trauma to the hair shaft and skin.

IH can be considered a medical condition, but as long as the substances employed to treat IH are not dermally resorbed into the body to become systemically active, the preparations fall into the field of cosmetics. A topical cosmetic composition not resorbed systemically, reducing the hair diameter, color and rate of growth and not changing the appearance of the skin would be of benefit to women affected by unwanted body hair.

Relevant Literature

For wrinkles, the use of natural extracts and their fractions has found extensive use in cosmetics: resveratrol, WO04/026, 222, WO01/30314; *Glycine soja*, U.S. patent application nos. 2004/0191350, 2005/0048105, 2005/0112153; grape seed oil, WO01/17495; *Boswellia serrata*, U.S. patent application no. 2005/01213559 and WO00/0578393; and *Cocos nucifera*, U.S. Pat. No. 6,551,656. Fluridil has been previously employed in formulations useful in a variety of conditions where its effect on the skin receptors is desirable (U.S. Pat. No. 6,184,249, which is specifically incorporated by reference herein, Sovak et al., 2001 WO 01/58854; 2002 Dermatol Surg 28:678-85; Seligson et al., 2003 Drug Dev Res 59:292-306).

Relevant Literature

References of interest for treating wrinkles include U.S. Pat. Nos. 5,889,054, 6,139,829, and 1,180,133. A discussion of hormone replacement is found in Sator et al., 2004 *Exp Dermatol* 13 Suppl 4:36-40.

For IH, see Goodheart H., "Hirsutism: Pathogenesis and Causes," *Women's Health Prim Care* 2000, 3:329-37; Azziz R., "The evaluation and management of hirsutism," *Obstet Gynecol* 2003, 101:995-1007; Shenenberger D, Utecht L., "Removal of unwanted facial hair," *Am Fam Physician* 2002, 66:1907-11; and Dawber R P. "Guidance for the management of hirsutism," *Current Medical Research and Opinion*, 2005, 21:1227-1234(8). Also, D. Cousty-Berlin et al., "Preliminary Pharmacokinetics and Metabolism of Novel Non-steroidal Antiandrogens in the Rat: Relation of their Systemic Activity to the Formation of a Common Metabolite," *Steroid Biochem Molec Biol* 1994, 51:47-55, and Labrie et al., "Topical antiandrogenic steroids," US 2004/0224935, Nov. 11, 2004.

BRIEF SUMMARY OF THE INVENTION

A cosmetic preparation for application to the skin for treatment of hormone related characteristics employs substituted highly hydrophobic substances containing an alkarylpolyfluorocarbon, particularly a substituted phenyl, perfluoroacylamino-propanamide, with a physiologically acceptable lower alkanol as a vehicle, in conjunction with solubilizing additives, particularly refined vegetable oils and thereof derived triglyceride fractions, associated with the particular characteristic being treated. A facial care cosmetic preparation and its use for reducing or eliminating the female facial hair in hirsutism optionally employs a moisturizing agent. A facial care cosmetic preparation and its use for reducing wrinkles employs, in addition to the above, a mixture of natural extracts or fractions thereof and optionally conventional additive(s) particularly antioxidants.

The preparations are substantially transparent non-irritating liquids which topically applied are rapidly resorbed into the skin to provide for the reduction of wrinkles and/or hirsutism. The preparations are not appreciably systemically resorbed.

BRIEF DESCRIPTION OF THE DRAWINGS

None.

DETAILED DESCRIPTION OF THE PREFERRED EMBODIMENT

Facial care cosmetic preparations are provided. These compositions comprise an effective amount of a highly hydrophobic substance comprising an alkaryl polyfluorocarbon, particularly a substituted phenyl, perfluoroacylamino-propanamide, in conjunction with other components providing for auxiliary benefits and solubility, a lower alkanol and at least one refined oil, fraction thereof, and optionally an antioxidant. (By effective amount is intended a sufficient amount to provide a therapeutic effect.) The vehicle will comprise a major amount of at least one refined vegetable oil and an oil triglyceride fraction and a minor amount of a physiologically acceptable alkanol of from 2-3 carbon atoms. The refined oil and its triglyceridic fractions will be present in major amount in the facial cosmetic composition, generally at least about 50 wt. %, more usually at least about 60 wt. %, and may be up to about 95 wt. %. The refined oil will be vegetable oils such as grape seed, rapeseed, soybean oils and at least one of oil fractions of *Cocos nucifera* ($C_{6-10}$ triglycerides) and/or *Glycine soja* (soybean oil, medium chain triglycerides). For wrinkle reduction, the composition will comprise at least one, usually a combination, of plant natural extracts or fractions thereof, or synthetic composition equivalents, at least one antioxidant, but may be a mixture of two or more antioxidants, e.g., vitamins, and, as appropriate, other additives. For facial hair reduction, the antioxidant will usually be tocopherol and optionally a moisturizing agent will be included.

The preparations are at least substantially homogeneous. They are readily applied to the skin as a substantially transparent liquid where it does not cause irritation. The compositions can be used safely, repeatedly. The preparations are not resorbed systemically. The alkaryl polyfluorocarbon compound employed will preferably be a substituted phenyl, perfluoroacylaminopropanamide. For the most part, the phenyl substituents will be 4-nitro-3-trifluoromethyl. Compounds of particular interest are 4-nitro-3-trifluoromethylphenyl substituted perfluoroacylaminopropanamide, wherein the perfluoroacyl group is of from 2-3 carbon atoms and said propanamide group is substituted at the 2-carbon atom with at least one of hydroxyl and methyl.

Compounds of particular interest are also described in U.S. Pat. Nos. 6,184,249 and 6,472,415, referenced above. In particular, these compounds comprise substituted phenylalanines comprising of a 2-hydroxyl, 2-methylpropionyl and a polyfluoroamido group. These compounds include those of the formula

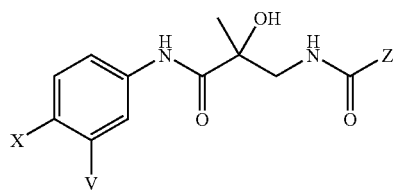

Formula I

Wherein:

X is nitro ($NO_2$), cyano (CN), or halogen, preferably F, Cl and Br, more preferably fluorine and chlorine, most preferably fluorine;

V is $CX_3$, where X is halogen preferably F, Cl and Br, more preferably fluorine and chlorine, and V is most preferably $CF_3$;

Z is $(CF_2)_n CF_3$ where n is 0 to 9, preferably 0 to 5, most preferably 0 to 2. These compounds bind specifically to the androgen receptor and have activity in blocking hormone receptors, preferably hormone receptors in the skin (e.g. androgen receptors) diminution of androgen receptors on the surface of cells and low systemic resorption when administered topically, while being topically active.

The compounds may or may not have one or more stereoisomeric centers. The compounds may be used as racemic mixtures or be resolved in their enantiomers and used as enantiomers.

The subject compounds can be prepared in accordance with conventional ways, varying the particular procedure based on the particular side groups. A suitable synthetic method is described in Seligson et al. Drug Dev. Res. 59:292-306.

The subject composition for wrinkle reduction employs effective amounts of a variety of physiologically acceptable natural extracts or fractions thereof, where these compositions have salutary effects for the skin and/or can serve in providing for a substantially uniform composition. Extracts that find application include Japanese knotweed, frankincense, non-saponifiable fractions from vegetable oils such as *Brassica oleifera* (turnip, rape) and *Glycine soja* fractions, as a supply of phytoestrogens. In addition, free radical scavengers are used, either synthetic or natural, particularly the antioxidant vitamins, Vitamins A and E.

For hirsutism, moisturizing agents include high molecular weight fatty acid esters of at least about 18 carbon atoms and up to 40 carbon atoms. Various types of moisturizers can be used that fall into a variety of classes. Occlusive ingredients include petrolatum, mineral oil, paraffin, squalene, vegetable fats (cocoa butter), animal fats (lanolin), lanolin acid, stearic acid, lanolin alcohol, cetyl alcohol, phospholipids, silicones, etc. Humectants include glycerin, propylene glycol, urea, sodium lactate, sorbitol, pyrrolidone carboxylic acid, etc. Emollients include octyl dodecanol, hexyl dodecanol, oleyl alcohol, oleyl oleate, octyl stearate, PEG-7, glycerol cocoate, myristyl myristate, isopropyl myristate, stearyl isononanoate, isopropyl palmitate, or isopropyl stearate.

Physiologically acceptable preservatives may also be used in the compositions, primarily for storage purposes to inhibit the oxidation of the susceptible ingredients, e.g., BHT, BHA (a mixture of the isomers 3-tert-butyl-4-hydroxyanisole and 2-tert-butyl-4-hydroxyanisole), TBHQ (tert-butylhydroquinone), ethoxyquin (6-ethoxy-1,2-dihydro-2,2,4-trimethyl quinoline), propyl gallate (gallic acid, propyl ester), tocopherol, rosemary extract, etc.

To varying degrees, other substances having substantially the same properties for the purpose of these compositions may be substituted for the specific compositions employed. These components will be used in an effective amount to provide the skin improvement and particularly the reduction in wrinkles or any hair except scalp hair.

The following table indicates the categories of material and the ranges in the skin care wrinkle reducing composition.

TABLE 1

| Component | Broad Range parts by weight | Narrow Range Parts by weight |
|---|---|---|
| phenyl-polyfluoroalkylamidopropanamide e.g., 2-hydroxy-2-methyl-N-[4-nitro-3-(trifluoromethyl)phenyl]-3-(2,2,2-trifluoroacetylamino) propanamide (fluridil) | 0.5-5 | 1-4 |
| Natural extracts | 0.5-5 | 0.75-3 |
| Japanese knotweed (resveratrol) | 0.1-2 | 0.2-1 |
| *Boswellia serrata* (60-70% triterpenes) | 0.1-2 | 0.2-1 |
| *Brassica oleifera* and/or *Glycine soja* (unsaponifiable fractions, phytoestrogens) | 0.1-2 | 0.2-1 |
| Refined oils | 50-95 | 60-95 |
| Grape seed oil (refined) | 25-60 | 30-50 |
| *Cocos nucifera* oil, medium chain triglyceride fractions (refined) | 30-65 | 35-60 |
| Antioxidants | 2-10 | 3-7 |
| Vitamin A | 0.5-4 | 0.5-2 |
| Vitamin E | 1-5 | 2-5 |
| Organic polar solvent (e.g., rubbing alcohol) | 2.5-10 | 3-7.5 |
| Preservatives | 0-0.5 | 0.05-0.2 |

The following table indicates the categories of material and the ranges in the hirsutism reducing composition.

TABLE 2

| Component | Broad Range parts by weight | Narrow Range Parts by weight |
|---|---|---|
| phenyl-polyfluoroalkylamidopropanamide e.g., 2-hydroxy-2-methyl-N-[4-nitro-3-(trifluoromethyl)phenyl]-3-(2,2,2-trifluoroacetylamino)propanamide (fluridil) | 0.5-5 | 1-4 |
| Refined oils | 80-95 | 85-95 |
| *Glycine soja* (refined) | 25-60 | 30-50 |
| *Cocos nucifera* oil, medium chain triglyceride fractions (refined) | 30-65 | 35-60 |
| Moisturizer | 0-2 | 0-1.5 |
| Antioxidants | 1-7 | 2-6 |
| Vitamin E | 1-5 | 2-5 |
| Organic polar solvent (e.g., rubbing alcohol) | 2.5-10 | 3-7.5 |
| Preservatives | 0-0.5 | 0.05-0.2 |

The subject compositions can be prepared using various protocols and orders of addition. For the wrinkle reduction compositions, conveniently, a first mixture (A) is prepared in the polar solvent heated to a range of about 50 to 80° C., preferably 60° C. to which the natural extract components is added sequentially and stirred until dissolved, e.g., resveratrol followed by the *Olibanum* extract. The mixture is stirred until completely homogenous and set aside. To the stirred *Cocos nucifera* oil triglyceride fraction (refined) at a mildly elevated temperature, generally in the range of about 35-50° C., is added the phenyl-perfluoroacylaminopropanamide and the mixture agitated for sufficient time to provide homogeneity, usually 20 minutes is adequate. To this mixture is then added the vegetable oil and the antioxidant preservative, followed by the vitamins. After stirring until the mixture appears homogeneous, the previously prepared mixture (A) is added dropwise with agitation to provide a concentrate that can be stored at below room temperature in a dark container.

For the hirsutism compositions, the phenyl-perfluoroacylaminopropanamide is added to the polar solvent and the mixture agitated for sufficient time to provide homogeneity, usually about 20 minutes. To this mixture are then added the vegetable oils and their triglyceride fractions, as appropriate, the antioxidant preservative, followed optionally by the antioxidant, e.g., tocopherol. If a moisturizing agent is desired, it is added slowly, e.g., dropwise, with agitation to provide a final mixture that can be stored at below room temperature in a dark container.

Various precursor compositions can be prepared having fewer than all of the components and the components added subsequently.

As distinct from other formulations, the subject formulations are usually at least substantially free of hydroxyacids and in the case of the wrinkle composition also free of monocarboxylic acid esters finding use in other cosmetic compositions.

Either the extracts or fractions thereof or the known active ingredient(s) may be used. Because of the economics, usually it will be preferred to use the natural extracts as the source of the active ingredient(s), rather than a substantially pure form, either obtained from a natural source or synthetic. The form of the extract used, when the active ingredient is known, will have at least about 50 wt. % of the active ingredient, and may have 70 wt. % or more. The equivalent composition obtained from a different source will have at least about 50%, usually at least about 70%, of the individual or mixture of the major component(s) of the natural extract or fraction thereof.

The phenyl-polyfluoroacylaminopropanamides are described in U.S. Pat. No. 6,184,249. The active compounds that may be employed are substances, which affect the skin androgen receptors but are not appreciably resorbed systemically. Such compounds are exemplified by 2-hydroxy-2-methyl-N-[4-nitro-3-(trifluoromethyl)phenyl]-3-(2,2,2-trifluoroacetylamino)propanamide(fluridil).

In the case of Japanese knotweed extract, the extract will usually have at least about 90% of trans-resveratrol (CAS No.: [501-36-0], 3,4',5-trihydroxy-trans-stilbene, as a glycon (Piceid). Any other source of resveratrol may be used that provides at least a substantially equivalent amount of resveratrol. Synthetically prepared resveratrol is also acceptable.

The extract from frankincense, *Boswellia serrata*, is a terpenoid mixture having from about 60-70% of triterpenes, the major portion of which are boswellic acids, of which at least 10 to 30% (wt/wt) is β-boswellic acid, 5 to 20% (wt/wt) is acetyl-β-boswellic acid, 5 to 20% (wt/wt) is 11-keto-β-boswellic acid and 5 to 20% (wt/wt) is acetyl-β-keto-β-boswellic acid (CAS No. [8050-07-5]). These extracts have found extensive use as food supplements and in cosmetics as reported in the literature for a wide variety of indications, with many anecdotal reports of success.

The phytoestrogens are readily available as a fraction derived from the vegetable oils rape-seed (*Brassica*) and/or soya (*Glycine soja*). In the subject formulation, the unsaponifiable fraction (CAS No. [91770-67-1]) of the appropriate vegetable oil is used as a source of phytoestrogens and will be substantially free of esters.

The grape seed oil (*Vitis vinifera*) or the soybean oil is primarily a mixture of saturated and unsaturated fatty acids having as its main constituents linoleic and oleic acids (>80%). These acids could be used independently of the other ingredients or the mixture prepared synthetically. They are used in their refined form.

Coconut oil (*Cocos nucifera*) provides primarily medium chain triglycerides where the acids are primarily $C_{6-10}$ saturated fatty acids, particularly caprylic and capric (CAS [73398-61-5]). It is used in its refined form.

Various antioxidants may be used that are conventionally found in cosmetic formulations. Vitamins A and E in their commercially available forms are favored, since they also are known to provide salutary physiological effects on the skin, but other antioxidants may also be employed, such as compounds having phenolic hydroxy functions, ascorbic acid and its derivatives/esters; beta-carotene; catechins; curcumin; ferulic acid derivatives (e.g., ethyl ferulate or sodium ferulate); gallic acid derivatives (e.g., propyl gallate); lycopene; reductic acid; rosmarinic acid; tannic acid; tetrahydrocurcumin; tocopherol derivatives; uric acid; or any mixtures thereof. Other suitable antioxidants are those having one or more thiol (—SH) functions, in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. These antioxidants may be used in partial or complete replacement of the vitamins and the antioxidant preservative, and for the vitamins, usually partial if at all, and will generally be present in less than 50% of the amount indicated for the vitamins, usually less than 30% indicated for the vitamins, generally being present to up to about 2 parts, more usually not more than about 1 part, while for the antioxidant preservative, they may be used as a complete replacement.

An alkanol is used of from 2-3 carbon atoms, e.g., ethanol, propylene glycol and isopropanol, particularly the latter in an amount to provide at least substantial homogeneity to the formulation.

Also usually included will be preservatives in minor amount, usually not more than about 3 different preservatives. The antioxidants described above may serve as preservatives. More conventionally BHT, BHA, TBHQ, ethoxyquin, propyl gallate, and rosemary extract is employed.

A particularly important aspect of this invention is the preferred formulation as described in the experimental section. The ingredient combination is formulated to solubilize all substances in a cosmetically acceptable medium. Several components, but particularly the extracts from *Boswellia serrata*, as well as the Japanese knotweed extract, are highly insoluble in customary systems. The combination forms a homogenous solution in the subject mixture of medium chain triglycerides (caprylic/capric triglycerides) with fractions of purified grape seed oil and the addition of a minimal amount (less than 10%) of rubbing alcohol (isopropanol).

The resulting mixture is a viscous liquid of oily appearance, which nevertheless becomes invisible on the skin within a short time after its topical application: the skin surface is not oily and the overall effect is that of high skin pliability and smoothness.

In addition to the above-enumerated ingredients, there may be other additives that are included for specific purposes. These additives and adjuvants are conventional in the cosmetic, pharmaceutical or dermatological field, such as hydrophilic or lipophilic gelling agents, hydrophilic or lipophilic active agents, solvents, fragrances, fillers, bactericides, odor absorbers and dyestuffs or colorants. The amounts of these various additives and adjuvants are those conventionally used in the field, and, for example, range from 0.01% to 10% of the total weight of the composition.

Emulsifiers that may be used include glyceryl stearate, polysorbate 60, PEG-6/PEG-32/glycol stearate mixture, etc.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

Suitable fatty alcohols and acids include those compounds having from 10 to 20 carbon atoms. Especially preferred are such compounds such as cetyl, myristyl, palmitic and stearyl acids and alcohols. Among the polyols, which may serve as emollients, are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also useful.

Exemplary hydrocarbons, which may serve as emollients, are those having hydrocarbon chains anywhere from 12 to 30 carbon atoms. Specific examples include mineral oil, petroleum jelly, squalene, and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

The subject compositions will be stored in containers that may be protected from light, by being opaque to incident light and may be sealed to minimize the oxygen present in the empty space. In light of the compositions cosmetic nature, the containers will be attractive, may have various shapes and come in a variety of sizes. The subject compositions may be supplied in conjunction with other skin formulations, as appropriate. The subject preferred compositions are characterized as being transparent liquids when applied to the skin. They are not absorbed systemically to any degree that can be found in the vascular system. They are found to have none to very low acute irritation potential in standard tests, and are safe for use with humans or other mammals. They have antimicrobial activity against a variety of organisms, inhibiting the growth of microorganisms in the composition. They have been found to be effective by subjective and objective tests, being described by users as providing a moisturizing and lifting sensation. Mapping and depth measurement of periocular/temporal wrinkles by laser profilometry shows a smoothing effect on the cutaneous microrelief, revealed by a decrease in the median depth of microrelief furrows and a significant decrease in the complexity in a majority of the subjects.

With a group of test subjects to provide a p value of less that 0.1, over about 50 days the volume of the wrinkles as measured by laser profilometry will be reduced in at least about 60 to 80, more usually at least about 70% of the subjects, and the depth of the wrinkle is reduced about 8-15%, and most usually by at least 10%.

In a clinical study employing the composition of Example 1 (although the compositions of Examples 8 and 9 would be anticipated to act at least as effectively), in 9 out of ten facially hirsute women who used in absence of any other treatment the composition herein described, as 2 ml massaged once a day into the affected areas, a substantial thinning, loss of color and reduced face and neck hair growth were documented.

The following examples are offered by way of illustration and not by way of limitation.

EXPERIMENTAL

Example 1

A typical composition 100 g of the novel skin care cosmetic preparation

| | |
|---|---|
| 0.5 g | extract from Japanese knotweed (mm. 95% trans-resveratrol); 3,4′,5-trihydroxytrans-stilbene, CAS No.: [501-36-0] |
| 0.5 g | extract from frankincense (Olibanum) - *Boswellia serrata* (60-70% triterpenes) CAS No.: [8050-07-5] |
| 0.5 g | extract from vegetable oil *Brassica oleifera/Glycine soja* (unsaponifiable fractions CAS [91770-67-1] |
| 3.0 g | vitamin E (DL-α-tocopherol acetate); 3,4-dihydro-2,5,7,8-tetramethyl-2-(4,8,12-trimethyltridecyl)-2H-1-benzopyran-6-ol acetate, 3.000 IU CAS No.: [7695-91-2] |
| 1.2 g | vitamin A (retinol palmitate); 3,7-dimethyl-9-(2,6,6-trimethyl-1-cyclohexen-l-yl)-2,4,6,8-nonatetraen-1-ol palmitate, 2,000.000 IU, CAS No.: [79-81-2] |
| 2.0 g | fluridil CAS No.: [260980-89-0] |
| 0.1 g | BHT (butylhydroxytoluene), 2,6-Di-tert-butyl-4-methylphenol CAS No.: [128-37-0] |
| 5.0 g | rubbing alcohol (isopropanol), CAS No.: [67-63-0] |
| 40.0 g | refined oil from grape seed, CAS No.: [8024-22-4] |
| 47.2 g | refined oil (*Cocos nucifera*) Caprylic/Capric middle chain triglycerides |

Example 2

Ocular Toxicity

Effects on the Ocular Fibroblasts

Rabbit corneal fibroblasts, to which Neutral Red is added in vitro, are exposed to the product at 15, 25 and 50% concentrations for 1 minute. The cell viability is measured by Optical Density. The culture medium serves as negative control. IC50 less than 50% was found, indicating that the product has a very low toxicity towards ocular mucous membranes, and is equivalent to the marketed products of the same category.

Example 3

Evaluation of the Antimicrobial Properties

The test, according to USP XXV, is based on inoculating the product with 5 strains, i.e., *S. aureus, P. aeruginosa, E. coli, C. albicans* and *A. niger*, incubation at 20° C. with the counts performed at 7, 14, 21 and 28 days. The antimicrobial ("preserving") efficiency of the product is considered positive when at day 14 the bacterial counts (measured by concentration CFU/g) are reduced by at least 2 logs and in the following 14 days continue to drop or stay equal to the starting counts. For yeasts/moulds the counts must be equal or lower at day 14 and 28, compared to the initial count.

TABLE 3

| SOUCHES/STRAINS | CONCENTRATIONS MEASURED (CFU/g) | | | | |
|---|---|---|---|---|---|
| | IN-OCULUM | J7/D7 | J14/D14 | J21/D21 | J28/D28 |
| S. aureus | 1.90E+07 | 0.00E+00 | 0.00E+00 | 0.00E+00 | 0.00E+00 |
| P. aeruginosa | 2.30E+07 | 0.00E+00 | 0.00E+00 | 0.00E+00 | 0.00E+00 |
| E. coli | 1.10E+07 | 0.00E+00 | 0.00E+00 | 0.00E+00 | 0.00E+00 |
| C. albicans | 2.20E+07 | 0.00E+00 | 0.00E+00 | 0.00E+00 | 0.00E+00 |
| A. niger | 3.10E+07 | 0.00E+00 | 0.00E+00 | 0.00E+00 | 0.00E+00 |

The product thus meets the USP XXV criteria as efficiently preserving the bacterial and fungal sterility.

Example 4

Mutagenicity Determination In Vivo

The test is standard to detect possible cytogenetic damage, which induces the formation of micronuclei containing lagging chromosomes or their fragments. To this end, the preparation was administered topically to three dose groups (0.5, 1.5 and 4.5 ml/kg, 5 male and 5 female per group) of SKH-1 mice, once daily for 28 days. Peripheral blood was sampled at 36 and 48 hours after the last administration and the reticulocytes were analyzed for the presence or absence of micronuclei after staining.

No increase in the frequency of micronucleated polychromatic erythrocytes was detected and the product therefore judged non-mutagenic.

Example 5

48-Hours Single Patch Test in Volunteers

The composition intended for wrinkles was evaluated as an open study on 11 adult volunteers, after a single application to the skin in the scapular area, under a semi-occlusive patch for 48 hours. The observations aimed at detecting erythema+edema were used to calculate the acute irritation index (M.I.I.) according to the standard formula to rank the cosmetic product according to the scale: M.I.I<0.20 Non-irritant (NI); 0.20–M.I.I<0.50 Slightly irritant (SI); 0.50–M.I.I<1 Moderately irritant (MI); M.I.I≧1 Irritant (I).

The product was classified as NI, non-irritant.

Example 6

Safety and Efficacy after 28 and 56 Days in Volunteers

On day 0, 28 and 56 in 24 volunteers,
a. Cutaneous safety was assessed by clinical exam by the dermatologist aimed at detecting signs of irritation such as erythema, edema, and urticaria. No significant findings were reported.
b. Laser Profilometry was carried out on a predetermined skin area and its wrinkles, to determine maximal or average depth, complexity, volume and isotropy. A precision captor is used, operating without surface contact to assess the geometric parameters of the wrinkle and the global skin area microrelief.

The data consists of complexity of the surface (or visual impact of a wrinkle in %), —maximum depth of the wrinkle (in mm), —volume of the wrinkle (in $mm^3$) and is analyzed by a paired t-test with significance limit of $p \leq 0.05$.

The findings are summarized in the following table:

TABLE 4

| | | % of volunteers with positive effect | Δ % from the mean | Mean ± SEM Δ (Day test – Day 0) | Student t-test p | significance |
|---|---|---|---|---|---|---|
| Complexity (in %) | Day 28 | 70% | −15% | −2.7 ± 1.2 | 0.035 | Yes |
| | Day 56 | 67% | −17% | −3.6 ± 2.5 | 0.164 | No |
| Maximum depth of the wrinkle (in mm) | Day 28 | 75% | −11% | −0.046 ± 03017 | 0.015 | Yes |
| | Day 56 | 72% | −11% | −0.071 ± 0.035 | 0.061 | Limit of significance |
| Volume (in $mm^3$) | Day 28 | 70% | −8% | −0.09 ± 0.04 | 0.031 | Yes |
| | Day 56 | 61% | −12% | −0.20 ± 0.09 | 0.054 | Limit of significance |

In conclusion, the product has shown a distinct tendency to reduce the wrinkles after 28 days and after 56 days. The objective findings were paralleled with the subjective reports of the volunteers.

Example 7

Preparation of 100 g of the Anti-Wrinkle Composition

To 5.0 g propan-2-ol at 60° C. is added 0.5 g extract of *Polygonum* (90-95% resveratrol glycon) CAS 501 36 0 and stirred till dissolved, then 0.5 g of the *Olibanum* extract is added, dissolved and the solution set aside (sol. A).

To 47.2 g of the coconut oil medium-chain triglyceride fraction at 40° C. is added 2.0 g fluridil (CAS 260980-89-0) and stirred for 20 minutes. 0.5 g of the vegetable oil extract (unsaponifiable fraction) and 0.1 g of BHT are added followed by 3.0 g vitamin E and 1.2 g vitamin A. The mixture is stirred until homogenous and sol. A is then added dropwise, under stirring. The resulting solution serves as a stock concentrate, which can conveniently be kept under nitrogen in closed dark containers, at max 15° C.

Final formulation is prepared by addition of 40 g of grape seed oil to the stock concentrate, to make 100 g of "CARE: the solution for the face" product.

Examples of anti-hirsutism compositions:

Example 8

| A typical 100 g composition applicable to hirsutism* |
| --- |
| 1.0 g oleyl oleate (octadec-9-enoic acid octadec-9-enyl ester) CAS [3687-45-4] |
| 3.0 g vitamin E (DL-α-tocopherol acetate); 3,4-dihydro-2,5,7,8-tetramethyl-2-(4,8,12-trimethyltridecyl)-2H-1-benzopyran-6-ol acetate, 3.000 IU CAS No.: [7695-91-2] |
| 2.0 g fluridil CAS No.: [260980-89-0] |
| 5.0 g rubbing alcohol (isopropanol), CAS No.: [67-63-0] |
| 41.5 g soybean oil, CAS No.: [8001-22-7] |
| 47.5 g refined oil (Cocos nucifera) Caprylic/Capric middle chain triglycerides |

*All items other than fluridil are listed in the FDA "Inactive Ingredients Database for Approved Drug Products" (http://www.accessdata.fda.gov/scripts/cder/iig/index.cfm).

Example 9

| A typical 100 g composition of the cosmetic oil applicable to hirsutism* |
| --- |
| 2.0 g fluridil CAS No.: [260980-89-0] |
| 6.0 g rubbing alcohol (isopropanol), CAS No.: [67-63-0] |
| 42.0 g soybean oil, CAS No.: [8001-22-7] |
| 50.0 g refined oil (Cocos nucifera) Caprylic/Capric middle chain triglycerides |

*All items other than fluridil are listed in the FDA "Inactive Ingredients Database for Approved Drug Products" (http://www.accessdata.fda.gov/scripts/cder/iig/index.cfm).

Example 10

Skin Composition Tested in Clinical Hirsutism

Ten females with face hirsutism from 25 to 68 years old were enrolled at the Department of Dermatology, Palacky University Hospital, Olomouc, Czech Republic. On day 0, photographic documentation of the affected area and blood samples were obtained for serum total testosterone and sex hormone binding globulin (SHBG). The subjects were instructed to apply 2 ml of product as a thin layer over the affected area (upper lip, chin, as appropriate) daily, in the evening. On day 90, there were no changes in the hormonal parameters, and the two dermatologists who independently evaluated the images concurred that hair growth, coloration and diameter were substantially reduced in 9 subjects. There were no local or systemic side effects.

It is evident from the above results that the subject compositions provide for improved skin care. The compositions serve in reducing wrinkles and the ravages of age, sun and toxic substances, including smoking, and reduce unwanted facial hair growth. The compositions are safe, using components that have been shown to be acceptable to humans. Despite using a mixture of hydrophobic and hydrophilic substances, a substantially homogeneous mixture is obtained that is readily applied to the skin to provide a transparent layer. The subject compositions can be used repeatedly without irritation to the skin or damage to the skin.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating wrinkles in a subject, said method comprising:
   topically applying an effective amount of a skin care composition of cosmetically acceptable components to the subject, said composition, comprising as its active ingredients:
   a physiologically acceptable 4-nitro-3-trifluoromethylphenyl substituted perfluoroacylaminopropanamide having a perfluoroacyl group and a propanamide group, wherein said perfluoroacyl group is from 2-3 carbon atoms and said propanamide group is substituted at the 2-carbon atom with at least one of hydroxyl and methyl;
   a vehicle comprising at least one refined oil, a triglyceride oil fraction, and an alkanol of from 2-3 carbon atoms, for providing a homogeneous mixture;
   an effective amount of at least one physiologically acceptable antioxidant; and
   said skin care composition further comprises a mixture of at least 3 extracts or fractions thereof, selected from the group consisting of a Japanese knotwood extract, a frankincense extract, and an unsaponifiable fraction of Brassica oleifera and/or Glycine soja.

2. A method according to claim 1, further comprising refined oils wherein the refined oils are from grape seed and from Cocos nucifera.

3. A method according to claim 1, wherein said antioxidants are vitamins.

4. A method according to claim 1, wherein said alkanol is isopropanol.

5. A method according to claim 1, wherein said 4-nitro-3-trifluoromethylphenyl substituted perfluoroacylaminopropanamide is 2-hydroxy-2-methyl-N-[4-nitro-3-(trifluoromethyl)phenyl]-3-(2,2,2-trifluoroacetylamino)propanamide.

6. A method according to claim 5 wherein said refined oil comprises 50-95 parts per weight of the skin care composition and consists of a mixture of at least two of: refined grape seed oil, Cocos nucifera oil medium chain triglyceride fraction, and an unsaponifiable fraction of Glycine soja.

7. A method according to claim 5 comprising 1 to 4 parts by weight of said 2-hydroxy-2-methyl-N-[4-nitro-3-(trifluoromethyl)phenyl]-3-(2,2,2-trifluoroacetylamino)propanamide.

8. A method of skin care for treating wrinkles in a subject, said method comprising:
   topically applying an effective amount of a skin care composition of cosmetically acceptable components to the subject, said composition, comprising as its active ingredients in parts by weight:
   0.5-5 parts of 2-hydroxy-2-methyl-N-[4-nitro-3-(trifluoromethyl)phenyl]-3-(2,2,2-trifluoroacetylamino)propanamide;
   0.1-2 parts of an extract from Japanese knotweed;
   0.1-2 parts of an extract from frankincense;
   0.1-2 parts of an unsaponifiable fraction of Brassica oleifera and/or Glycine soja;
   50-95 parts of refined oils from at least one of grape seed and Cocos nucifera, medium chain triglyceride fractions;

2-10 parts of the antioxidants Vitamin A and Vitamin E;
2.5-10 parts of an alkanol of from 2-3 carbon atoms for providing a homogeneous mixture; and
0-0.5 parts of preservatives.

9. A method according to claim 8, wherein said alkanol is isopropanol.

10. A method according to claim 8, wherein both grape seed and *Cocos nucifera* medium chain triglyceride fractions are present.

11. A method according to claim 8, comprising as its active ingredients in parts by weight:
   1-4 parts of 2-hydroxy-2-methyl-N-[4-nitro-3-(trifluoromethyl)phenyl]-3-(2,2,2-trifluoroacetylamino)propanamide;
   a total of 0.75-3 parts of extracts of Japanese knotweed, frankincense, and an unsaponifiable fraction of at least one of *Brassica oleifera* and *Glycine sofa;*
   30-50 parts of refined grape seed oil;
   35-60 parts of refined *Cocos nucifera* oil medium chain triglyceride fraction;
   3-7 parts of antioxidants; and
   3-7.5 parts of an alkanol of from 2-3 carbon atoms for providing a homogeneous mixture.

12. A method according to claim 8 wherein said topically applying is applying said composition as a transparent liquid.

13. A method of skin care for treating wrinkles in a subject, said method comprising:
   topically applying an amount of a skin care composition of cosmetically acceptable components effective to treat wrinkles to the subject, said skin care composition comprising in parts by weight:
   1-4 parts of 2-hydroxy-2-methyl-N-[4-nitro-3-(trifluoromethyl)phenyl]-3-(2,2,2-trifluoroacetylamino)propanamide;
   a total of 0.75-3 parts of an extract or fraction thereof, selected from the group consisting of an extract from Japanese knotweed, an extract from frankincense, and an unsaponifiable fraction of at least one of *Brassica oleifera* and/or *Glycine soja;*
   30-50 parts of refined grape seed oil;
   35-60 parts of refined *Cocos nucifera* oil medium chain triglyceride fractions;
   3-7 parts of antioxidants; and
   3-7.5 parts of an alkanol of from 2-3 carbon atoms, for providing a homogeneous mixture.

14. A method according to claim 13 wherein said applying is done at least daily for 28 days.

\* \* \* \* \*